United States Patent
Keibel

(10) Patent No.: US 11,660,245 B2
(45) Date of Patent: May 30, 2023

(54) HIPPOTHERAPY DEVICE

(71) Applicant: KUKA Deutschland GmbH, Augsburg (DE)

(72) Inventor: Andreas Keibel, Augsburg (DE)

(73) Assignee: KUKA Deutschland GmbH, Augsburg (DE)

( * ) Notice: Subject to any disclaimer, the term of this patent is extended or adjusted under 35 U.S.C. 154(b) by 1147 days.

(21) Appl. No.: 16/321,224

(22) PCT Filed: Jul. 19, 2017

(86) PCT No.: PCT/EP2017/068186
§ 371 (c)(1),
(2) Date: Jan. 28, 2019

(87) PCT Pub. No.: WO2018/019672
PCT Pub. Date: Feb. 1, 2018

(65) Prior Publication Data
US 2019/0159952 A1    May 30, 2019

(30) Foreign Application Priority Data

Jul. 28, 2016   (DE) ...................... 10 2016 213 964.9

(51) Int. Cl.
*A61H 1/00*  (2006.01)
*A63B 69/04*  (2006.01)
(Continued)

(52) U.S. Cl.
CPC ................ *A61H 1/003* (2013.01); *A61B 5/11* (2013.01); *A61H 1/001* (2013.01);
(Continued)

(58) Field of Classification Search
CPC .......... A61H 1/001; A61H 1/003; A61H 3/00; A61H 3/008; A63B 69/04; A63B 26/003;
(Continued)

(56) References Cited

U.S. PATENT DOCUMENTS

| | | | | |
|---|---|---|---|---|
| 3,997,979 A | * | 12/1976 | Turner | A63B 69/04 434/247 |
| 4,861,021 A | * | 8/1989 | Edwards | A63B 21/4009 482/54 |
| 4,898,378 A | * | 2/1990 | Edwards | A63B 22/0235 482/69 |

(Continued)

FOREIGN PATENT DOCUMENTS

| | | |
|---|---|---|
| CN | 1727020 A | 2/2006 |
| CN | 201052392 Y | 4/2008 |

(Continued)

OTHER PUBLICATIONS

European Patent Office; Search Report in related International Patent Application No. PCT/EP2017/068186 dated Sep. 27, 2017; 2 pages.

(Continued)

*Primary Examiner* — Justine R Yu
*Assistant Examiner* — Christopher E Miller
(74) *Attorney, Agent, or Firm* — Dorton & Willis, LLP

(57) ABSTRACT

A hippotherapy device includes a saddle for receiving a person thereon, a programmable movement control, and an automatic movement device for automatically moving the saddle according to a movement pattern program. The program specifies a sequence of target values of positions and orientations of the saddle in the locality of the movement device in order to execute the movement pattern. The hippotherapy device further includes a person securing device having a main support on which a body strap is mounted, at least one sensor for detecting at least one physical variable characterizing the body posture of the person on the saddle, and an auxiliary control device configured to compare expected values of the physical variable with current values of the physical variable detected by the sensor, and to trigger an associated safety function, if a (Continued)

deviation of the current values from the expected values exceeds a predetermined tolerance threshold.

16 Claims, 3 Drawing Sheets

(51) Int. Cl.
  *A63B 69/00* (2006.01)
  *A63B 71/00* (2006.01)
  *A61B 5/11* (2006.01)
  *A63B 21/005* (2006.01)
  *A63B 24/00* (2006.01)
  *B25J 9/16* (2006.01)
  *A63B 21/00* (2006.01)
  *A61B 5/00* (2006.01)
  *A63B 21/008* (2006.01)
  *A63B 21/02* (2006.01)

(52) U.S. Cl.
  CPC .... *A63B 21/0058* (2013.01); *A63B 21/00178* (2013.01); *A63B 24/0087* (2013.01); *A63B 69/0057* (2013.01); *A63B 69/0064* (2013.01); *A63B 69/04* (2013.01); *A63B 71/0054* (2013.01); *B25J 9/1664* (2013.01); *A61B 5/742* (2013.01); *A61B 5/7405* (2013.01); *A61B 2505/09* (2013.01); *A61H 2201/0176* (2013.01); *A61H 2201/0184* (2013.01); *A61H 2201/1633* (2013.01); *A61H 2201/1652* (2013.01); *A61H 2201/1659* (2013.01); *A61H 2201/5007* (2013.01); *A61H 2201/5061* (2013.01); *A61H 2201/5064* (2013.01); *A61H 2201/5069* (2013.01); *A61H 2201/5084* (2013.01); *A61H 2203/0425* (2013.01); *A61H 2230/62* (2013.01); *A61H 2230/625* (2013.01); *A63B 21/0083* (2013.01); *A63B 21/0087* (2013.01); *A63B 21/02* (2013.01); *A63B 21/4007* (2015.10); *A63B 2024/0012* (2013.01); *A63B 2024/0093* (2013.01); *A63B 2071/0018* (2013.01); *A63B 2071/0081* (2013.01); *A63B 2220/10* (2013.01); *A63B 2220/16* (2013.01); *A63B 2220/18* (2013.01); *A63B 2220/30* (2013.01); *A63B 2220/40* (2013.01); *A63B 2220/51* (2013.01); *A63B 2220/805* (2013.01)

(58) Field of Classification Search
  CPC ............... A63B 71/0054; A63B 22/18; A63B 2208/0233; A63B 69/0064
  See application file for complete search history.

(56) References Cited

U.S. PATENT DOCUMENTS

| | | | | |
|---|---|---|---|---|
| 5,085,425 A * | 2/1992 | Collins | A63G 19/20 | 472/97 |
| 5,704,881 A * | 1/1998 | Dudley | A63B 21/00181 | 482/69 |
| 6,234,800 B1 * | 5/2001 | Koyama | A63B 26/003 | 434/61 |
| 6,488,640 B2 * | 12/2002 | Hood, Jr. | A61H 1/003 | 472/95 |
| 6,616,456 B1 * | 9/2003 | Nalty | A63B 69/04 | 472/59 |
| 6,808,458 B1 * | 10/2004 | Jung | A63B 69/04 | 434/247 |
| 7,070,415 B2 * | 7/2006 | Hojo | A63B 26/003 | 472/59 |
| 7,104,927 B2 * | 9/2006 | Tsai | G09B 9/00 | 472/95 |
| 7,121,831 B2 * | 10/2006 | Hojo | A63B 69/04 | 434/247 |
| 7,338,413 B2 * | 3/2008 | Nakanishi | A63B 21/0058 | 472/59 |
| 7,347,806 B2 * | 3/2008 | Nakano | A63B 24/00 | 434/247 |
| 7,354,382 B1 * | 4/2008 | Warren, II | A61H 3/04 | 482/68 |
| 7,608,017 B2 * | 10/2009 | Nakanishi | A63B 26/003 | 482/52 |
| 7,670,230 B2 * | 3/2010 | Hsu | A61H 1/001 | 434/247 |
| 7,775,939 B2 * | 8/2010 | Nakanishi | A61H 1/001 | 482/4 |
| 7,785,234 B2 * | 8/2010 | Nakanishi | A63B 69/04 | 434/247 |
| 7,828,705 B2 * | 11/2010 | Nakano | A63B 69/04 | 482/142 |
| 7,931,565 B2 * | 4/2011 | Nakano | A63B 69/04 | 434/247 |
| 9,360,093 B2 * | 6/2016 | Garner | A63B 21/0058 | |
| 10,478,371 B2 * | 11/2019 | Stockmaster | G16H 40/63 | |
| 11,202,934 B2 * | 12/2021 | Kim | A63B 69/0062 | |
| 2002/0025889 A1 * | 2/2002 | Egger | A63B 22/0605 | 482/57 |
| 2002/0026130 A1 * | 2/2002 | West | A61H 1/0262 | 601/23 |
| 2002/0058891 A1 * | 5/2002 | Hood, Jr. | A61H 1/003 | 601/26 |
| 2002/0082535 A1 * | 6/2002 | Eaves | A61H 1/001 | 601/99 |
| 2002/0115536 A1 * | 8/2002 | Hojo | A63B 26/003 | 482/148 |
| 2003/0153438 A1 * | 8/2003 | Gordon | A63B 69/0064 | 482/92 |
| 2004/0019304 A1 * | 1/2004 | West | A61H 1/0237 | 601/5 |
| 2005/0101448 A1 * | 5/2005 | He | A61H 1/0255 | 482/69 |
| 2006/0025226 A1 * | 2/2006 | Nakano | A63B 69/0053 | 472/100 |
| 2006/0052728 A1 * | 3/2006 | Kerrigan | A63B 21/00181 | 600/595 |
| 2006/0229170 A1 | 10/2006 | Ozawa et al. | | |
| 2007/0004567 A1 * | 1/2007 | Shetty | A61H 3/008 | 482/69 |
| 2007/0238579 A1 * | 10/2007 | Nakano | A63B 69/04 | 482/51 |
| 2007/0275358 A1 * | 11/2007 | Nakanishi | A63B 69/04 | 434/247 |
| 2008/0287268 A1 * | 11/2008 | Hidler | A61H 3/008 | 482/69 |
| 2009/0062075 A1 * | 3/2009 | Nakanishi | A63B 69/04 | 482/133 |
| 2010/0125024 A1 | 5/2010 | Nakano et al. | | |
| 2010/0190616 A1 * | 7/2010 | Imai | A61H 1/001 | 482/77 |
| 2010/0222191 A1 * | 9/2010 | Shinomiya | A63B 21/00181 | 482/142 |
| 2010/0234196 A1 * | 9/2010 | Shinomiya | A63B 21/00178 | 482/142 |
| 2010/0240507 A1 * | 9/2010 | Shinomiya | A63B 21/068 | 482/142 |
| 2010/0265090 A1 * | 10/2010 | Bisset | A47C 7/725 | 340/573.7 |
| 2011/0312473 A1 * | 12/2011 | Chu | A63B 24/0006 | 482/54 |
| 2013/0045812 A1 * | 2/2013 | Garner | A63G 19/20 | 472/97 |
| 2013/0116604 A1 * | 5/2013 | Morilla | A63G 9/12 | 601/33 |
| 2014/0087922 A1 * | 3/2014 | Bayerlein | A63B 21/00181 | 482/54 |
| 2014/0093851 A1 | 4/2014 | Kim et al. | | |

(56) References Cited

U.S. PATENT DOCUMENTS

| | | | |
|---|---|---|---|
| 2015/0306440 A1* | 10/2015 | Bucher | A63B 22/0023 |
| | | | 482/4 |
| 2016/0256346 A1* | 9/2016 | Stockmaster | G16H 40/63 |
| 2016/0296405 A1 | 10/2016 | Oshima et al. | |
| 2016/0346156 A1* | 12/2016 | Walsh | A61H 3/008 |
| 2017/0056275 A1* | 3/2017 | Lee | A61H 1/0255 |
| 2017/0072266 A1* | 3/2017 | Sasaki | A63F 13/214 |
| 2017/0165145 A1* | 6/2017 | Aryananda | A61H 3/04 |
| 2018/0050252 A1* | 2/2018 | Ye | A63B 71/0622 |
| 2019/0183715 A1* | 6/2019 | Kapure | G16H 50/20 |

FOREIGN PATENT DOCUMENTS

| | | |
|---|---|---|
| CN | 101732830 A | 6/2010 |
| CN | 101797428 A | 8/2010 |
| CN | 105764465 A | 7/2016 |
| EP | 1629868 A1 | 3/2006 |
| JP | 2001286578 A | 10/2001 |
| JP | 4270113 B2 | 5/2009 |
| KR | 100782550 B1 | 12/2007 |
| KR | 101415462 B1 | 7/2014 |
| WO | 2012119176 A2 | 9/2012 |

OTHER PUBLICATIONS

Chinese Patent Office; Office Action in related Chinese Patent Application No. 201780046692.5 dated Jun. 3, 2020; 6 pages.
Chinese Patent Office; Search Report in related Chinese Patent Application No. 201780046692.5 dated May 29, 2020; 3 pages.
Chinese Patent Office; Office Action in related Chinese Patent Application No. 201780046692.5 dated Nov. 9, 2020; 3 pages.

* cited by examiner

HIPPOTHERAPY DEVICE

CROSS-REFERENCE TO RELATED APPLICATIONS

This application is a national phase application under 35 U.S.C. § 371 of International Patent Application No. PCT/EP2017/068186, filed Jul. 19, 2017 (pending), which claims the benefit of priority to German Patent Application No. DE 10 2016 213 964.9, filed Jul. 28, 2016, the disclosures of which are incorporated by reference herein in their entirety.

TECHNICAL FIELD

The invention relates to a hippotherapy device, comprising a saddle, which constitutes a seat for a person, as well as a programmable movement control and an automatic movement device designed to automatically move the saddle according to a movement pattern program that is to be executed by the movement control and that specifies a sequence of target values of positions and orientations of the saddle in the locality of the movement device, in order to execute the movement pattern.

BACKGROUND

A therapy robot is known from WO 2012/119176 A2. On a base unit having connected controller, a robot arm, which can be moved by means of multiple pivot joints, i.e., articulated joints, is attached therein on a truck. It is thus possible to position and orient an end effector of the therapy robot, which end effector is similar in its shape to a part of the back region of a horse, arbitrarily in space in a specific region.

SUMMARY

The object of the invention is to provide a hippotherapy device, in the case of which a person using the hippotherapy device can be conditioned and/or treated using teaching and/or therapy methods, in particular in a particularly safe manner.

The object of the invention is achieved by a hippotherapy device, comprising a saddle, which constitutes a seat for a person, as well as a programmable movement control and an automatic movement device designed to automatically move the saddle according to a movement pattern program that is to be executed by the movement control and that specifies a sequence of target values of positions and orientations of the saddle in the locality of the movement device, in order to execute the movement pattern, and comprising a person securing device, which comprises a main support on which a body strap is mounted, at least one sensor designed to detect at least one physical variable characterizing the body posture of the person on the saddle, and an auxiliary control device designed to use the expected values of the physical variable, which characterize the expected body posture of the person on the saddle, in accordance with the movement pattern program and the position and orientation of the saddle, to compare set expected values to the current values of the physical variable detected by the sensor, which characterize the actual body posture of the person on the saddle, and to trigger an associated safety function, if a deviation of the current values of the physical variable from the expected values of this physical variable exceeds a predetermined tolerance threshold.

The movement pattern program can automatically specify the movements of the saddle provided for a time window, which movements correspond to the movements desired by the therapy method. The movement pattern program is thus predetermined by the therapist of the hippotherapy device.

The expected values are values of physical variables, which represent the body posture of the person on the saddle, specifically the body posture which the person would be expected to assume or is supposed to assume under safe, normal conditions, as the current movement of the saddle is supposed to correspond according to the movement pattern program.

The tolerance threshold defines deviations of the values from the expected values, which no longer precisely correspond to the expected body posture of the person on the saddle but are nonetheless within a scope which characterizes a still safe state of the person on the saddle.

The physical variable characterizing the body posture of the person on the saddle can be the spatial position and/or the spatial orientation of the upper body, the head, at least one arm, and/or at least one leg of the person.

The safety function to be triggered can be stopping of the movement device and/or outputting a signal characterizing the unsafe state of the person on the saddle. Stopping of the movement device can be carried out in that the motors or drives of the movement device are stopped and the saddle thus assumes a fixed position in space and accordingly no longer moves. In the event of stopping of the movement device, the person can still be held in a safe position by means of the body strap and the main support. In particular, upon stopping of the movement device, the person can be protected from falling down or slipping off of the saddle by means of the body strap and the main support.

Outputting a signal characterizing the unsafe state of the person on the saddle can be carried out by the auxiliary control device generating a signal and the hippotherapy device comprising a display means, on which the signal is output. The display means can comprise a lighting means, an acoustic output means, a display screen, on which an item of information characterizing the unsafe state of the person is displayed, and/or a transmitting unit and a receiving unit. The transmitting unit can in this case transmit an item of information characterizing the unsafe state of the person and the receiving unit can comprise a display means, a display screen, or an acoustic output means, such as a loudspeaker, on which the item of information characterizing the unsafe state of the person is output. The receiving unit can be, for example, a mobile telephone, a pager, or a personal pager. A continuous presence of a therapist during the therapeutic operation of the hippotherapy device is no longer uninterruptedly necessary due to an information output which characterizes the unsafe state of the person. Rather, the movement control can run the movement device automatically according to the movement pattern program to be executed, in particular a therapy guideline, without a therapist having to be present. However, the therapist can immediately be called thereto automatically in an unsafe state.

Instructions can also be automatically given directly to the person seated on the saddle, as to what the person is to do in order to end or resolve the unsafe state, with the output of a signal characterizing the unsafe state of the person on the saddle, in an acoustic manner in automatically spoken words or sentences, or in a visual manner in automatically displayed texts or sentences.

The safety function to be triggered can alternatively or additionally also be an activation of at least one actuator, which acts on the spatial position and/or the spatial orientation of the upper body, the head, at least one arm, and/or at least one leg of the person.

The hippotherapy device can accordingly comprise at least one actuator, which is designed to automatically act on the body strap, which is adjustably mounted on the main support, with respect to its spatial pose, wherein the auxiliary control device is designed to activate the at least one actuator in dependence on the current position and movement of the saddle and the current body posture of the person on the saddle. By means of the at least one actuator, the person can be moved, for example, back into a position, orientation, and/or body posture or prompted to assume a position, orientation, and/or body posture again themselves, in which the person reassumes or has the body posture on the saddle expected on the basis of the movement pattern program.

The saddle, which forms a riding seat for a person, can simulate a real riding saddle, as is typically designed for riding horses. However, the saddle can also be formed reduced to its fundamental functions. The fundamental functions are such that the saddle has to be designed in such a way that a person can sit thereon in an at least approximately upright posture and the two legs of the person can each hang down respectively on the left and right laterally of the saddle, i.e., the seat surface of the saddle. Optionally, the saddle can possibly also have stirrups, on which the person can support himself with his two feet, as is also typical when riding horses. In a very simple embodiment, however, the saddle can already be formed solely by a substantially cylindrical main body, which is arranged having its cylinder axis oriented essentially horizontally, so that the lateral surface of the cylindrical main body is used as a seat surface for the person. The two legs of the person then hang down on the left and right laterally to the cylindrical main body.

The programmable movement control can comprise a robot, in particular an industrial robot, on the robot flange of which the saddle is arranged as an end effector. The programmable movement control can accordingly comprise a robot arm and a programmable robot control.

Robot arms having associated programmable robot controls, in particular industrial robots, are working machines which can be equipped for automatic handling and are programmable in multiple movement axes, for example, with respect to orientation, position, and work sequence. Industrial robots typically comprise a robot arm having multiple links connected via joints and programmable robot controls (control devices), which automatically control and/or regulate the movement sequences of the robot arm during operation, in order to position and move a robot flange of the robot arm in space. The links are moved for this purpose via drive motors, in particular electric drive motors, which are activated by the robot control, in particular with respect to the movement axes of the industrial robot, which represent the degrees of movement freedom of the joints. The robot can be, for example, an industrial robot, which can be in particular an articulated arm robot having rotational axes following one another in series, for example, five, six, or seven rotational axes. The saddle of the hippotherapy device can accordingly be moved in space in that the joints of the robot arm are moved, i.e., adjusted, in a manner activated by the programmable robot control.

The predetermined movement pattern, which simulates riding movements, can be stored in the programmable movement control, in particular in the programmable robot control, and can be retrievable therefrom for execution. The predetermined movement pattern is executed by the programmable movement control moving the saddle by adjusting the joints, for example, of the robot arms, in the locality in order to simulate riding movements.

The person securing device is device different from the movement control and from the saddle, which is designed not to monitor and/or hold the seat, i.e., the pelvic region of the person, but rather is designed to monitor and/or hold the upper body of the person. The person securing device can accordingly comprise a body strap, which connects the main support of the person securing device to the upper body of the person. In this case, the body strap is mounted so it is adjustable on the main support. The body strap can be designed in the manner of a climbing harness or a rescue harness. The body strap can in particular comprise at least one chest belt, belly belt, and/or lap belt enclosing the person. The body strap can comprise, for example, a chest harness. Even if the person securing device is a device different from the movement control and from the saddle, the person securing device can optionally either be configured as a separate device on a floor or foundation or can be fastened to the movement control or to the saddle as an attached auxiliary device.

The person securing device is a device different from the movement control and from the saddle insofar as the person securing device comprises at least one independent actuator, which is separate from the drives of the automatically adjustable joints of the movement control. The at least one actuator can be an active actuator. The active actuator can be, for example, a drive or a motor. The at least one actuator can also be a passive actuator, however. The passive actuator can be, for example, a brake or a vibration damper, which influences, i.e., changes, a movement already applied to the person securing device.

An actuator is accordingly understood in the scope of the invention very generally as a component (or an assembly) which can in particular convert electrical signals into mechanical movement or into other physical variables. The mechanical movement can be a movement at constant velocity. However, the mechanical movement can also be in particular an acceleration or deceleration, i.e., a negative acceleration. A conversion into another physical variable can be, for example, as described in the scope of the invention, a damping of a vibration movement. An actuator is therefore understood as an actuator element, i.e., a drive element, which passively and/or actively influences the person securing device.

The auxiliary control device activates the at least one actuator, either to move the body strap mounted on the main support actively, i.e., by means of a drive and/or a motor, and/or to passively decelerate and/or brake an existing movement of the body strap with respect to the main support by braking and/or damping.

The auxiliary control device can communicate with the movement control, in particular with a programmable robot control.

According to the invention, the person or a patient can take a seat on the saddle of the hippotherapy device, which can form a hippotherapy system. After configuring a movement pattern, for example, a therapy, with the aid of a therapist, the therapy can be carried out without the further presence of the therapist.

In this case, the person is secured using the person holding device on the saddle, so that the person firstly cannot fall down. This can be implemented in various embodiments. For example, the person or the patient can reach the therapy place together with the therapist. The therapist helps the patient onto the saddle. Thereafter, the therapist secures the patient against slipping down and/or falling down by means of the person holding device. The therapist subsequently configures the therapy and/or selects an existing movement pattern for application and starts the therapy procedure.

The person holding device can in particular comprise the following characteristics against the patient falling down from the therapy seat. Since the patient is moved during the therapy, the person holding device, i.e., the body strap, cannot be designed as rigid and spatially fixed, but rather has to follow the person or the patient at least approximately without force.

If the patient threatens to lose his therapy position, i.e., for example, slips from the saddle, the holding device can become active and prevent the further slipping down, without the patient thus feeling pain or other damage or another risk resulting.

If the patient does not return back into an upright position after a possibly settable time, the person holding device can thus, for example, trigger an alarm and order a therapist, so that the therapist can reestablish the proper state.

Such a securing and holding system can be equipped with sensors, which can actively and reliably monitor the patient posture on the saddle. This monitoring can take place in multiple steps and with the aid of various measured indices.

A strap system, which holds the patient on the upper body from above, can measure the tension force and/or distance which the patient exerts on the holder and/or by which the upper body is moved away from the upright posture, for example. Tensile force sensors, for example, weighing cells, installed in the straps can recognize an asymmetry and/or a load state, which can result in more extensive, posture-correcting movements of the movement device, in particular the robot arm. The robot can automatically execute a correction movement to orient the patient, in order to remind him to sit straight. If this is not successful, the therapy can then also be terminated and a therapist request can be initiated automatically.

The patient securing, which in particular encloses the upper body, can optionally measure the inclination of the shoulders and the spinal column, for example, by means of inclination sensors, so that imminent slipping down can be recognized early.

A hippotherapy device can implement various intelligent behavior methods, using which slipping of the person off of the saddle can be prevented, so that the patient does not slip with his entire weight into the holding device. If a posture error is recognized, for example, the therapy movement first becomes slower and is then interrupted entirely. A special movement of the saddle is possibly also activated, using which the patient is either reminded to sit straight, or he is mechanically oriented.

If the state does not then improve, by the patient attempting himself to reassume the correct posture, the person securing device can take active motorized countermeasures, for example, and execute a movement which attempts to orient the patient again, in the case of an actuated holding device. This therapy interruption causes an active perception of his posture problem in the patient.

If the state should not improve, the therapy can be interrupted and, for example, a request signal can be placed for the therapist, so that the therapist can take over the procedure and can decide whether the therapy can continue and if so, how.

The movement control, in particular the robot and/or the mechatronic system using which the saddle and/or the seat of the person or the patient is moved, can in particular comprise the following securing devices, which can be embodied in at least two channels.

The securing devices can comprise a Cartesian monitored workspace (entry, therapy height, width, and depth) embodied in safe technology, a secure Cartesian velocity and acceleration, a secure monitored workspace on the axial level, a secure monitored velocity on the axial level.

Several embodiment variants are explained in greater detail hereafter.

The main support can be fastened on a foundation, for example, on which the programmable movement device, in particular a base frame of a robot arm, is also fastened. The adjustable mounting of the body strap then enables a corresponding number of degrees of freedom, i.e., a corresponding number of degrees of mobility in at least one direction and/or at least one orientation in space in relation to the foundation, in particular in relation to the programmable movement device or in relation to the base frame of the robot arm.

The main support can also be fastened, however, on an adjustable link of the programmable movement device, in particular on a part of a robot arm or on the saddle, which is moved by the programmable movement device. The adjustable mounting of the body strap then enables a number of degrees of freedom, i.e., a number of degrees of mobility in at least one direction and/or at least one orientation in space in relation to the saddle or in relation to the flange of a robot arm.

The directions in space can be characterized by one, two, or three Cartesian coordinate systems and/or the one, two, or three orientations in space can each be the rotations around one of the three Cartesian coordinate directions.

In one embodiment variant, the body strap can be adjustably mounted on the main support by means of a bearing device or a bearing in at least one direction and/or at least one orientation in space and the bearing can comprise a braking device in this case, which is designed to brake a movement of the bearing using optionally different braking properties, which are settable by means of the actuator, specifically in a manner activated by the auxiliary control device. The actuator can accordingly influence the braking device, in particular activate it, or the actuator can itself be the braking device.

The braking device can be designed as automatically changeable with respect to its braking action. I.e., the level of the braking action can be automatically adjustable by the auxiliary control device. In particular, the auxiliary control device can automatically change the level of the braking action in the time curve, specifically in dependence on the current position and/or orientation of the body strap.

The braking device can be associated with the bearing device or the bearing, respectively. The bearing can be a pivot bearing and/or a slide bearing. The braking device can comprise brake linings, for example, which are automatically adjustable and can be pressed with normal forces of different levels against a brake disc. The braking device can be configured to brake at least or solely an adjustment of the bearing because of gravity influences. Alternatively or additionally, the braking device can also be configured to decelerate a driven bearing set into motion.

In another, alternative or additional embodiment variant, the body strap can be mounted on the main support in a vibrating manner in at least one direction and/or at least one orientation in space by means of a bearing device or a bearing and the bearing can comprise a vibration damping device in this case, which is designed to damp a movement of the bearing using optionally different vibration damping properties, which are settable by means of the actuator, specifically activated by the auxiliary control device. The actuator can accordingly influence the vibration damping device, in particular activate it, or the actuator can itself be the vibration damping device.

The mounting or the bearing can be formed in this case, for example, by a spring device. The spring device can comprise, for example, a spring coil having a fixed spring stiffness. The spring device can also comprise, for example, an oil pressure spring or gas pressure spring, the spring stiffness of which can be settable. The actuator can thus activate, for example, a throttle device of the oil pressure spring or gas pressure spring or can be this throttle device.

The vibration damping device can be combined with the braking device.

In a further, alternative or additional embodiment variant, the body strap can be mounted on the main support so it can be driven in at least one direction and/or at least one orientation in space by means of a drive device and the drive device can comprise at least one motor in this case, which forms the actuator and which is designed to move the body strap in an automatically driven manner, specifically activated by the auxiliary control device.

The drive device can comprise at least one motor, which is configured to automatically adjust the bearing device or the bearing, respectively. The actuator can accordingly influence, in particular activate, the drive device or the at least one motor, respectively, or the actuator can itself be the drive device or the at least one motor, respectively. The at least one motor can thus be driven by the auxiliary control device, for example, in particular driven in different rotational velocities and rotational directions and in particular also decelerated.

The drive device can be combined with the braking device and/or with the vibration damping device.

In all embodiment variants, the hippotherapy device can comprise at least one sensor, which is designed to detect the spatial position and/or the spatial orientation of the body of the person.

The sensor does not necessarily have to be fastened directly on the body of the person or on the body strap in this case. Rather, the sensor can also be arranged separately, isolated from the body of the person and isolated from the body strap, and can remotely detect the spatial position and/or the spatial orientation of the body of the person. The sensor can thus be formed, for example, by an optical sensor, such as a camera, which optically detects the spatial position and/or the spatial orientation of the body of the person, and generates associated image data, wherein the image data can be analyzed to numerically determine the current spatial position and/or the spatial orientation of the body of the person.

In one special embodiment, however, the body strap can comprise the at least one sensor. In this special embodiment, the sensor can then, for example, comprise at least one attitude sensor and/or one acceleration sensor, which is designed to detect the current attitude of the body strap and/or the current movement of the body strap. The accurate position and attitude of the body of the person can then be concluded from the current attitude of the body strap and/or the current movement of the body strap, in particular via a time curve of the attitude of the body strap and/or the movement of the body strap.

In general, the at least one sensor can be connected via a communication connection to the auxiliary control device, in such a manner that items of information about the current position and/or current orientation of the body of the person in space are transmitted to the auxiliary control device, in order to automatically determine the current body posture of the person by means of the auxiliary control device or the movement control.

The at least one sensor can accordingly communicate in a wired or wireless manner with the auxiliary control device. A communication can insofar already be provided solely by a transfer or transmission of measured values of the at least one sensor to the auxiliary control device. The at least one sensor does not necessarily also have to be configured to receive items of information or data from the auxiliary control device. The at least one sensor can also simply be electrically connected in a similar manner to the auxiliary control device.

In a first embodiment, the body strap can be mounted suspended on the main support by means of a support cable and the hippotherapy device can comprise an angle transducer in this case, which is designed to detect the angular position of the support cable. The angular position of the support cable can comprise a first angle component in this case, which defines the deflection angle of the support cable in relation to the vertical direction, and can comprise a second angle component, which defines the direction of the deflection of the support cable. The support cable can have a fixed support cable length. Alternatively, the support cable can be designed as variable in length.

In a second, alternative or additional embodiment, the body strap can accordingly be mounted suspended on the main support by means of a length-variable support cable and the hippotherapy device can comprise a length transducer in this case, which is designed to detect the current length of the support cable.

The length-variable support cable can comprise, for example, a cable pulley, on which a first partial length of the support cable is stored rolled up. A second partial length of the support cable, which is not stored rolled up on the cable pulley, forms a free, variable cable length, the current length of which can be detected by means of the length transducer.

In a third, alternative or additional embodiment, the body strap can be mounted suspended on the main support by means of a support cable and the hippotherapy device can comprise a force transducer in this case, which is designed to detect the tensile force on the support cable.

The force transducer can be arranged in particular on the person securing device. For example, the force transducer can be fastened on the main support and can be coupled to the support cable.

In one special embodiment, which can be provided alternatively or additionally to other embodiments, the body strap can comprise at least one first support strap section, which connects a body strap section of the body strap at a first connecting point of the body strap section to an attachment point of the support cable, and the body strap can comprise at least one second support strap section, which connects the body strap section at a second connecting point of the body strap section, which is different from the first connecting point, to the attachment point of the support cable, wherein the first support strap section has a first transducer, which detects at least one physical variable on the first support strap section, and the second support strap section has a second transducer, which detects at least one physical variable on the second support strap section. The at least one physical variable can be a force, a torque, a spatial position/orientation, a velocity, and/or an acceleration.

The first connecting point and the second connecting point can be arranged at a distance from one another, specifically at the same height on the support strap in the case of upright body posture, i.e., a symmetrically hanging support strap. For example, the first connecting point and the second connecting point can be arranged in the vicinity of the two shoulders of the person on the support strap. Because the first support strap section comprises a first transducer, which detects at least one physical variable on the first support strap section, and the second support strap section comprises a second transducer, which detects at least one physical variable on the second support strap section, the first transducer and the second transducer can establish from the detected physical variables, in particular from the deviation of the two values measured by the first transducer and the second transducer, whether the person is in an upright body posture or sits obliquely, and/or threatens to slip down from the saddle.

In all embodiments, the movement control can be configured to automatically modify the predetermined movement pattern to activate the movement device, in dependence on the action of the at least one actuator on the body strap adjustably mounted on the main support.

Various exemplary embodiments of the invention are illustrated by way of example in the appended schematic drawings. Specific features of these exemplary embodiments can represent general features of the invention independently of the specific context in which they are mentioned, possibly also individually or in combinations other than those illustrated.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
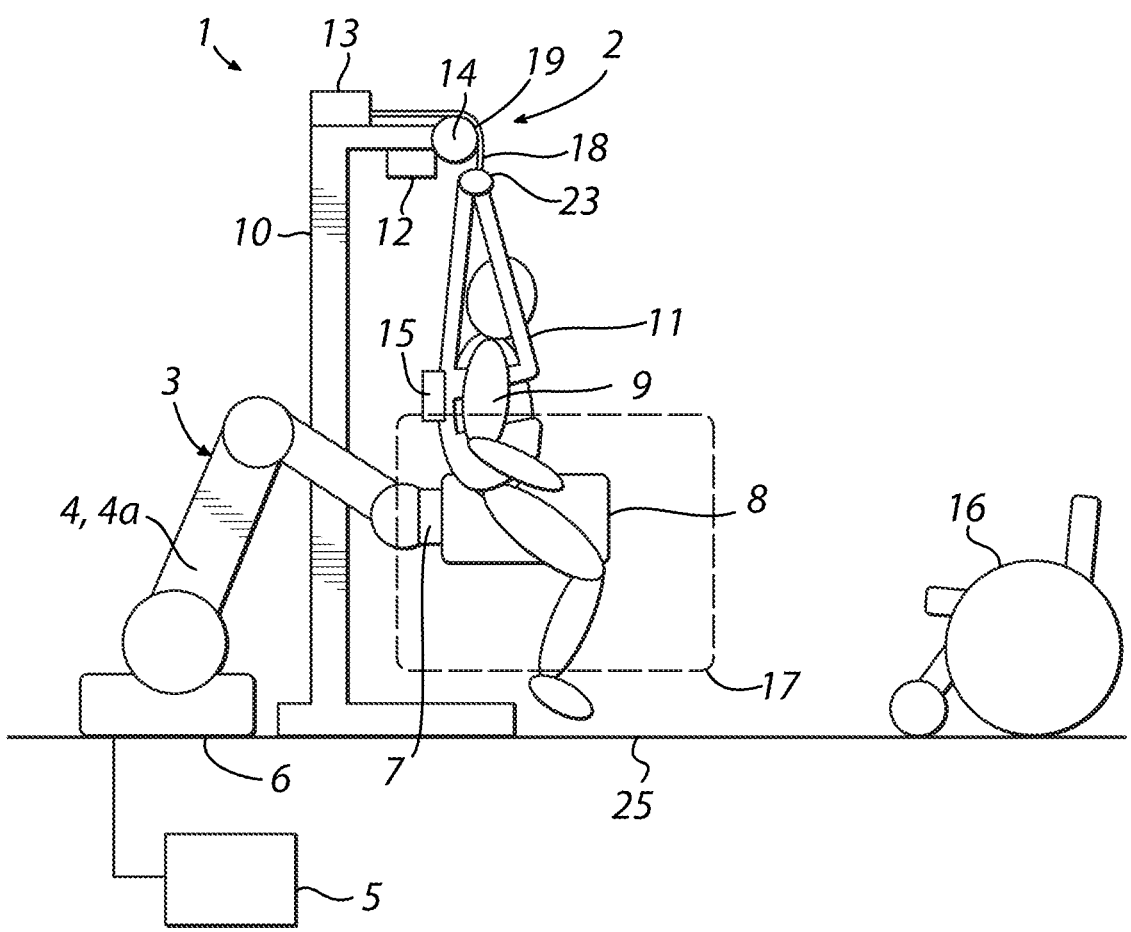
FIG. 1 shows a schematic illustration from the side of a first embodiment of the hippotherapy device according to the invention having a stationary person securing device.

FIG. 1 shows a first embodiment of a hippotherapy device 1 having a stationary person securing device 2.

The hippotherapy device 1 moreover comprises, in the case of the current exemplary embodiment, an industrial robot 3, which comprises a programmable movement control 5 and an automatic movement device 4. The automatic movement device 4 is formed in the case of the current exemplary embodiment by a robot arm 4a, having multiple links connected via joints. The robot arm 4a comprises, inter alia, a base frame 6 and a robot flange 7. A saddle 8 is fastened on the robot flange 7.

The robot arm 4a comprises multiple links connected via joints, wherein the programmable movement controller 5 is configured to automatically control and/or regulate the movement sequences of the robot arm 4a during operation, in order to position and move the robot flange 7 of the robot arm 4a and thus also the saddle 8 in space.

The hippotherapy device 1 accordingly comprises the saddle 8, which forms a riding seat for person 9. The hippotherapy device 1 additionally comprises the programmable movement control 5 and the robot arm 4a. The robot arm 4a is designed to automatically move the saddle 8 according to a movement pattern predetermined by the movement control 5.

The person securing device 2 comprises a main support 10, on which a body strap 11 is adjustably mounted. The person securing device 2 additionally comprises at least one actuator 12, which is designed to act on the body strap 11 adjustably mounted on the main support 10 with respect to its spatial pose, and an auxiliary control device 13, which is designed to activate the at least one actuator 12 in dependence on the current position and movement of the saddle 8 and the current body posture of the person 9 on the saddle 8.

The body strap 11 is adjustably mounted in at least one direction and/or at least one orientation in space on the main support 10 by means of a bearing 14 and the bearing 14 has a braking device in a first variant, which is designed to brake a movement, i.e., a rotation of the bearing 14, using optionally different braking properties, which are settable by means of the actuator 12, specifically activated by the auxiliary control device 13.

The body strap 11 can also be mounted on the main support 10 by means of the bearing 14 to vibrate in at least one direction and/or at least one orientation in space, wherein the bearing 14 has a vibration damping device, which is designed to damp a movement of the bearing 14 using optionally different vibration damping properties, which are settable by means of the actuator 12, specifically activated by the auxiliary control device 13.

The body strap 11 can also be mounted on the main support 10 so it is driven by means of a drive device in at least one direction and/or at least one orientation in space, wherein the drive device comprises at least one motor, which forms the actuator 12 and which is designed to move the body strap 11 in an automatically driven manner, specifically activated by the auxiliary control device 13.

The hippotherapy device 1 can comprise at least one sensor 15, which is designed to detect the spatial position and/or the spatial orientation of the body of the person 9.

In the case of the current exemplary embodiment, the at least one sensor 15 is arranged on the body strap 11 in the vicinity of the back of the person.

The person securing device 2 can also be used for the purpose of lifting the person 9 out of a wheelchair 16 and placing him on the saddle 8. In the same meaning, the person securing device 2 can also be used for the purpose of lifting the person 9 out of the saddle 8 and placing him back in the wheelchair 16.

The movement control 5, in particular the industrial robot 3 and/or the mechatronic system, using which the saddle 8 and/or the person 9 is moved, can in particular comprise a securing device, which can be embodied in at least two channels.

The securing device can comprise a Cartesian monitored workspace 17 embodied in secure technology, which can be defined by the entry and the therapy height, width, and depth. The securing device can comprise a secure Cartesian velocity and acceleration, a secure monitored workspace on the axial level, a secure monitored velocity on the axial level. The exemplary workspace 17 is schematically bounded by a rectangle shown by dashed lines in FIG. 1 and FIG. 2.

The at least one sensor 15 can be connected via a communication connection to the auxiliary control device 13, in such a manner that items of information about the current position and/or current orientation of the body of the person 9 in space are transmitted to the auxiliary control device 13, in order to automatically determine the current body posture of the person 9 by means of the auxiliary control device 13 or the movement control 5.

The body strap is mounted suspended on the main body 10 by means of a support cable 18 in the case of the illustrated exemplary embodiments and the hippotherapy device 1 comprises, for example, an angle transducer, which is designed to detect the angular position of the support cable 18.

Figure 2:
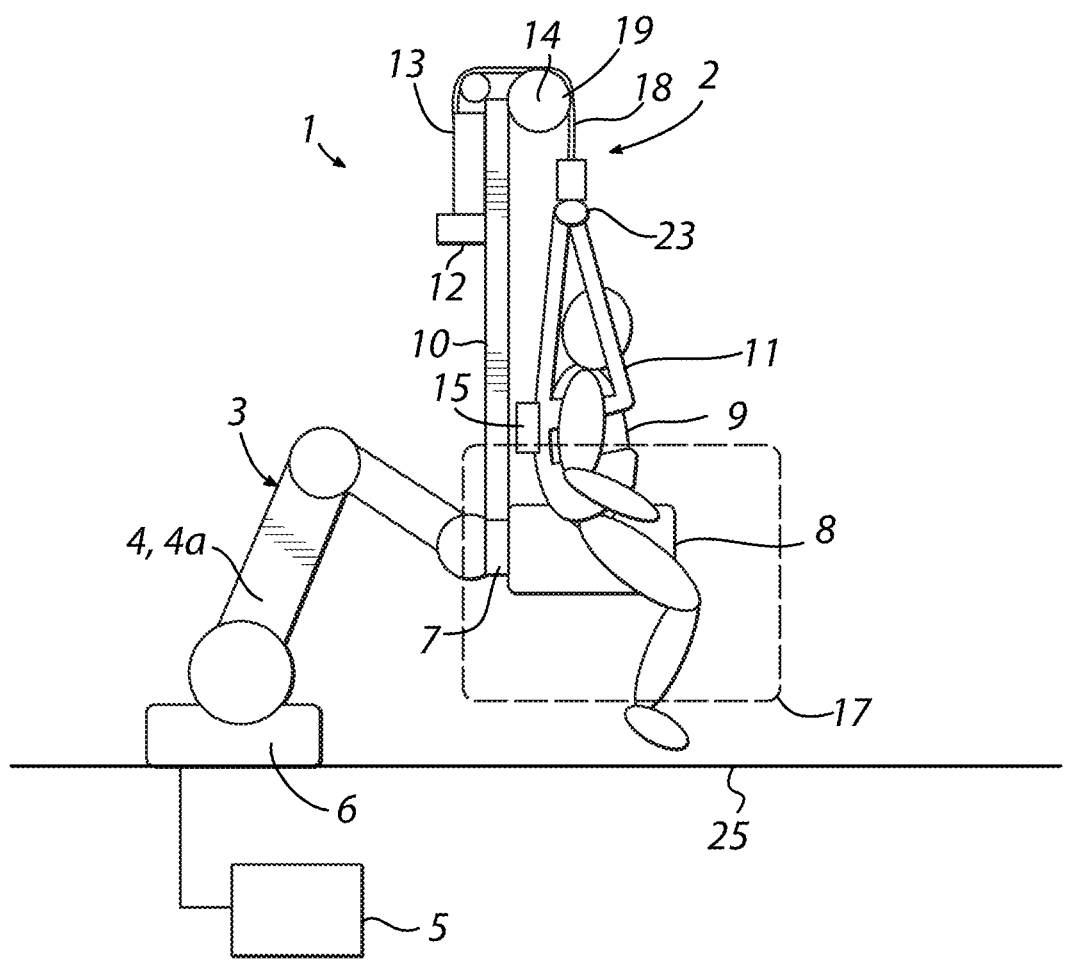
FIG. 2 shows a schematic illustration from the side of a second embodiment of the hippotherapy device according to the invention having a person securing device, which is fastened on a movement device of the hippotherapy device.

In this case, the angular position of the support cable 18 can comprise a first angle component, which defines the deflection angle of the support cable 18 in relation to the vertical direction, and can comprise a second angle component, which defines the direction of the deflection of the support cable 18. The support cable, as shown in FIG. 1 and FIG. 2, can be designed as variable in length via a cable pulley 19, for example.

If the body strap 11 is mounted suspended by means of a length-variable support cable 18 on the main body 10, the hippotherapy device 1 can also comprise a length transducer, which is designed to detect the current length of the support cable 18.

The hippotherapy device 1 can moreover comprise a force transducer, which is designed to detect the tensile force on the support cable 18.

In the case of the exemplary embodiment of FIG. 1, the main support 10 is fastened on a floor 25, on which the programmable movement device 4, in particular the base frame 6 of the robot arm 4a, is also fastened. The adjustable mounting of the body strap 11 then enables a corresponding number of degrees of freedom, i.e., a corresponding number of degrees of mobility in at least one direction and/or at least one orientation in space in relation to the floor 25, in particular in relation to the programmable movement device 4 or in relation to the base frame 6 of the robot arm 4a.

The main support 10 can also, however, as shown in FIG. 2, be fastened on an adjustable link of the programmable movement device 4, in particular on the robot flange 7 of the robot arm 4a or on the saddle 8, which is moved by the programmable movement device 4. The adjustable mounting of the body strap 11 then enables a number of degrees of freedom, i.e., a number of degrees of mobility in at least one direction and/or at least one orientation in space in relation to the robot flange 7 or in relation to the saddle 8.

Figure 3:
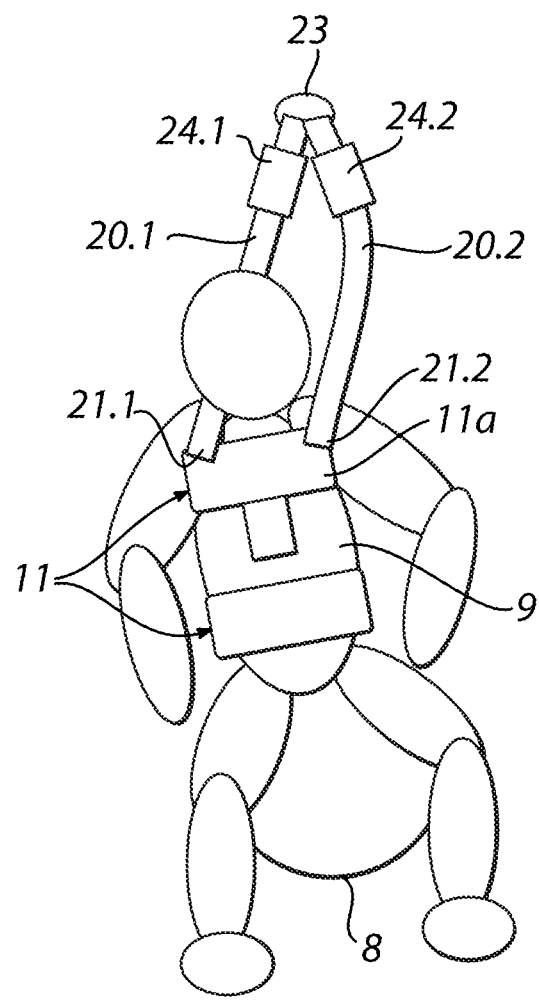
FIG. 3 shows a schematic illustration from the front of a hippotherapy device according to FIG. 1 or FIG. 2 having sensors which are arranged on a body strap of the person securing device.

As shown in particular in FIG. 3, the body strap 11 can comprise at least one first support strap section 20.1, which connects a body strap section 11a of the body strap 11 at a first connecting point 21.1 of the body strap section 11a to an attachment point 23 of the of the support cable 18, and the body strap 11 can comprise at least one second support strap section 20.1, which connects the body strap section 11a at a second connecting point 21.2, which is different from the first connecting point 21.1, of the body strap section 11a to the attachment point 23 of the support cable 18, wherein the first support strap section 20.1 comprises a first transducer 24.1, which detects at least one physical variable on the first support strap section 20.1, and the second support strap section 20.2 comprises a second transducer 24.2, which detects at least one physical variable on the second support strap section 20.2. The physical variable can be, for example, a tensile force in the first support strap section 20.1 and/or in the second support strap section 20.2.

The movement control 5 is configured in the exemplary embodiments shown to automatically modify the predetermined movement pattern to activate the movement device 4, in dependence on the action of the at least one actuator 12 on the body strap 11 adjustably mounted on the main support 10.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

What is claimed is:

1. A hippotherapy device, comprising:
a saddle defining a seat for a person;
a programmable movement controller;
an automatic movement device configured to automatically move the saddle according to a movement pattern program executed by the movement controller and that specifies a sequence of target values of positions and orientations of the saddle in the locality of the automatic movement device in order to execute the movement pattern; and
a person securing device, comprising:
a main support;
a body strap mounted on the main support,
at least one sensor configured to detect at least one physical variable characterizing a body posture of a person on the saddle, and
an auxiliary control device configured to use expected values of the at least one physical variable corresponding to the current position and orientation of the saddle in the movement pattern program, to compare the expected values to current values of the at least one physical variable detected by the at least one sensor, and to trigger an associated safety function if a deviation of the current values from the expected values exceeds a predetermined tolerance threshold.

2. The hippotherapy device of claim 1, wherein the physical variable characterizing the body posture of the person on the saddle is at least one of a spatial position or a spatial orientation of at least one of the upper body, the head, at least one arm, or at least one leg of the person.

3. The hippotherapy device of claim 1, wherein the safety function to be triggered is at least one of stopping the movement device or outputting a signal indicating an unsafe state of the person on the saddle.

4. The hippotherapy device of claim 1, wherein the safety function to be triggered is an activation of at least one actuator that acts on at least one of the spatial position or the spatial orientation of at least one of the upper body, the head, at least one arm, or at least one leg of the person.

5. The hippotherapy device of claim 1, wherein the at least one sensor is arranged on the body strap.

6. The hippotherapy device of claim 1, wherein the at least one sensor is connected via a communication connection to the auxiliary control device in such a way that items of information about at least one of the current position or current body posture of the body of the person in space are transmitted to the auxiliary control device such that the current body posture of the person can be automatically determined with the auxiliary control device or the movement controller.

7. The hippotherapy device of claim 1, wherein:
the body strap is mounted suspended on the main support by a support cable; and
the hippotherapy device further comprises an angle transducer configured to detect an angular position of the support cable.

8. The hippotherapy device of claim 1, wherein:
the body strap is mounted suspended on the main support by a length-variable support cable; and
the hippotherapy device further comprises a length transducer configured to detect a current length of the support cable.

9. The hippotherapy device of claim 1, wherein:
the body strap is mounted suspended on the main support by a support cable; and
the hippotherapy device further comprises a force transducer configured to detect a tensile force on the support cable.

10. The hippotherapy device of claim 1, wherein:
the body strap is mounted suspended on the main support by a support cable; and
the body strap comprises:
at least one first support strap section connecting a body strap section of the body strap, at a first connecting point of the body strap section, to an attachment point of the support cable, and
at least one second support strap section connecting the body strap section, at a second connecting point of the body strap section that is different from the first connecting point, to the attachment point of the support cable;
wherein the first support strap section comprises a first transducer configured to detect at least one physical variable on the first support strap section; and
the second support strap section comprises a second transducer configured to detect at least one physical variable on the second support strap section.

11. The hippotherapy device of claim 1, wherein the person securing device is adapted to follow a movement of the person on the saddle at least approximately without applying force to the person while the deviation is less than the tolerance threshold.

12. A hippotherapy device, comprising:
a saddle defining a seat for a person;
a programmable movement controller;
an automatic movement device configured to automatically move the saddle according to a movement pattern program executed by the movement controller and that specifies a sequence of target values of positions and orientations of the saddle in the space surrounding of the automatic movement device in order to execute the movement pattern; and
a person securing device, comprising:
a main support;
a body strap mounted on the main support,
at least one sensor configured to detect at least one physical variable characterizing a body posture of a person on the saddle, and
an auxiliary control device configured to use expected values of the at least one physical variable corresponding to the current position and orientation of the saddle in the movement pattern program, to compare the expected values to current values of the at least one physical variable detected by the sensor, and to trigger an associated safety function if a deviation of the current values from the expected values exceeds a predetermined tolerance threshold;
wherein the body strap is adjustably mounted on the main support; and
the hippotherapy device further comprises:
at least one actuator configured to automatically act on the body strap to vary a spatial pose of the body strap;
wherein the auxiliary control device is configured to control the at least one actuator based on a current position and movement of the saddle and a current body posture of the person on the saddle.

13. The hippotherapy device of claim 12, further comprising:
a bearing mounting the body strap on the main support, the bearing configured to adjust at least one of:
at least one direction of the body strap, or
at least one orientation of the body strap in space;
the bearing comprising a braking device configured to brake a movement of the bearing using selectable braking properties, the braking properties being settable by the actuator controlled by the auxiliary control device.

14. The hippotherapy device of claim 12, further comprising:
a bearing mounting the body strap on the main support for swinging movement thereon in at least one of:
at least one direction, or
at least one orientation of the body strap in space;
the bearing comprising a vibration damping device configured to damp a movement of the bearing using selectable damping properties, the damping properties being settable by the actuator controlled by the auxiliary control device.

15. The hippotherapy device of claim 12, further comprising:
a drive device on the main support and configured to drive movement of the body strap in at least one of:
at least one direction, or
at least one orientation of the body strap in space;
wherein the drive device comprises at least one motor that constitutes at least one of the at least one actuator, the drive device configured to move the body strap in an automatically driven manner, controlled by the auxiliary control device.

16. The hippotherapy device of claim 12, wherein the movement controller is configured to automatically modify a predetermined movement pattern for the activation of the movement device based on the action of the at least one actuator on the body strap.

* * * * *